United States Patent [19]

Röthlisberger et al.

[11] 4,405,645
[45] Sep. 20, 1983

[54] TREATMENT OF DANDRUFF WITH BIGUANIDES

[75] Inventors: Rudi Röthlisberger, Fribourg; Friedrich Noser, Bonnefontaine, both of Switzerland

[73] Assignee: Wella Aktiengesellschaft, Darmstadt, Fed. Rep. of Germany

[21] Appl. No.: 249,666

[22] Filed: Mar. 26, 1981

[30] Foreign Application Priority Data

Apr. 2, 1980 [DE] Fed. Rep. of Germany ....... 3012767

[51] Int. Cl.$^3$ ...................... A61K 7/06; A61K 31/155
[52] U.S. Cl. ..................................... 424/326; 424/70; 424/DIG. 4
[58] Field of Search ..................... 424/70, 71, 72, 326, 424/DIG. 4

[56] References Cited

FOREIGN PATENT DOCUMENTS 2611957 9/1977 Fed. Rep. of Germany .
702268 1/1954 United Kingdom .
1432345 4/1976 United Kingdom ................ 424/326

Primary Examiner—Albert T. Meyers
Assistant Examiner—Freda L. Abramson
Attorney, Agent, or Firm—Michael J. Striker

[57] ABSTRACT

Cosmetic agents for the control of head dandruff, containing customary cosmetic carrier substances and additives, and 1 to 5% by weight of salts of at least one biguanide derivative of the general formula

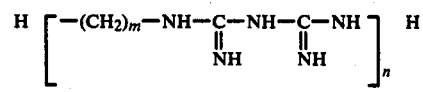

wherein m is from 1 to 10 and n is from 1 to 6. Preferred salts include oligohexamethylene biguanide, oligotetramethylene biguanide and 1-methyl biguanide. Also preferred are the hydrochloride salts of biguanide derivatives. The agents may be in the form of shampoos, hair lotions, hair setting preparations, rinses, hair dressing gels and creams, hair oils, powders, or sprays. Customary carrier substances may be an ointment base, a powder, water, alcohol or water-alcohol mixtures. Customary cosmetic additives include resins, emulsifiers, thickeners, hair care substances, coloring agents, perfume oils, solid fillers, and propellants.

5 Claims, No Drawings

TREATMENT OF DANDRUFF WITH BIGUANIDES

BACKGROUND OF THE INVENTION

The invention concerns cosmetic agents with a content of salts of monomeric or oligomeric biguanide derivatives for the control of head dandruff.

There are already numerous substances recommended as effective for the control of head dandruff. These include compounds which increase the flow of blood, such as nicotinic acid ester, and also panthenol, colloidal sulfur, hydroxyquinoline, phenol, quaternary ammonium compounds, selenium sulfide, pyridine thione, and numerous other compounds.

Of the known compounds the 1-hydroxy-2-pyridine thione and its salts, particularly the zinc salt, exhibit a particularly good effectiveness against head dandruff. Based on the limited solubility of the zinc pyridine thiones in the usual cosmetic solvents such as water and alcohol, they can however only with difficulty be worked up into clear cosmetic agents.

The compounds previously suggested as effective substances for treatment of head dandruff could with regard to their effectiveness against head dandruff in toxicological and dermatological respects or—such as in the case of the zinc pyridine thiones—on account of the difficult solubility in cosmetic solvents, not completely satisfactorily meet the necessary requirements.

There exists therefore the problem of making cosmetic agents available with a content of an effective substance for controlling head dandruff, which better fulfill the above mentioned requirements.

The antibacterial and antimycotic effectiveness of salts of oligomeric polymethylene biguanide is known from British Pat. No. 702,268. These salts have already been described, alone or in combination with other microbiocides, as being components of disinfectants (see German Offenlegungsschrift No. 2,611,957). Furthermore, the use of polyhexamethylene biguanide hydrochloride is known for preserving cosmetic emulsions. For the purpose of preservation the polyhexamethylene biguanide hydrochloride should be contained in an amount of about 0.06 to 0.3% by weight in the preserved preparation. Amounts of polyhexamethylene biguanide hydrochloride sufficient for preserving purposes in cosmetic preparations have, however, according to investigation not been determined to provide an effectiveness against head dandruff.

Compared to this it has been surprisingly discovered that hair and scalp treatment agents with a content of at least 1% by weight of salts of biguanide derivatives exhibit an excellent effectiveness against head dandruff. Moreover, with the use of these biguanide compounds as antidandruff effective substances, in comparison to zinc pyridine thione, clear cosmetic hair and scalp treatment agents may be produced without difficulty.

These clear cosmetic agents show, besides, a better physiological compatibility as such than a content of zinc pyridine thione.

SUMMARY OF THE INVENTION

The subject of the invention is therefore cosmetic agents, containing known cosmetic carriers and additives, characterized by a content of 1–5% by weight of salts of at least one biguanide derivative of the general formula $$H\left[-(CH_2)_m-NH-\underset{\underset{NH}{\|}}{C}-NH-\underset{\underset{NH}{\|}}{C}-NH\right]_n H$$

in which m is 1 to 10 and n is 1 to 6, for control of head dandruff.

As salts of the preceding mentioned biguanide derivatives, the chloride salts and the acetate salts, for example, come into consideration.

Examples of suitable salts of biguanide derivatives which may be contained in the agents according to the invention, and according to the formula, are the following: oligohexamethylene biguanide hydrochloride (with n=4 to 6) oligotetramethylene biguanide hydrochloride (with n=4 to 6) 1-methyl biguanide hydrochloride.

The production of such salts of biguanide derivatives has been known for a long time. Methods for production of oligomeric polymethylene biguanide salts are described, for example, in British Pat. No. 702,268, as follows:

We manufacture the said polymeric substances by a process which comprises reacting a bisdicyandiamide of the formula $$CN-NH-\underset{\underset{NH}{\|}}{C}-NH.X.NH-\underset{\underset{NH}{\|}}{C}-NH-CN$$

with a diamine of the formula $$NH_2-Y-NH_2$$

The two components are conveniently brought into reaction by heating together, the diamine being preferably used in the form of a salt thereof, preferably at temperatures between 100° C. and 170° C., either alone, or in the presence of a neutral medium.

According to yet a further feature of the invention we provide a process for the manufacture of those of the said polymeric substances in the structure of which X and Y are identical by a process which comprises interaction of equimolecular proportions of dicyanimide and a diamine of the formula $$NH_2-X^1-NH_2$$

where $X^1$ is a bridging group in which the total number of carbon atoms is greater than 4 and smaller than 9, the diamine being preferably in the form of a salt.

The salts of biguanide derivatives mentioned as components of the here described cosmetic agents display, in consideration of the recommended concentration for the agents according to the invention, an excellent effectiveness against head dandruff. In addition, they can, on account of their good solubility in the solvents customarily used for cosmetic preparations, such as water and water-alcohol mixtures, find use in most of the cosmetic forms of preparation.

The preceding described salts of biguanide derivatives should optionally find use in suitable cosmetic preparations for hair and scalp treatment such as, for example, hair setting preparations, rinses, hair dressing gels and creams, hair oils, powders, sprays, preferably however in shampoos and hair lotions.

These preparations, according to the purpose of use, should remain on the hair and the scalp for shorter or longer periods of time. Through their content of the described salts of biguanide derivatives, they will simultaneously bring about a dandruff treatment. It is, however, also possible to produce preparations which principally or exclusively serve the objects of a dandruff control.

The concentration of salts of biguanide derivatives according to the formula in the preparations which remain on the hair, such as, for example, in hair lotions and hair setting preparations, comes to about 1–5% by weight, preferably 1–2% by weight. Preparations which after a brief period according to their use are rinsed off, such as, by way of example, shampoos and rinses, contain the mentioned salts of biguanide derivatives in an amount of about 1–5% by weight, preferably 1–3% by weight. The compounds may be present alone or in mixture with one another in these preparations.

The components of these cosmetic preparations display a mixture of the salts of biguanide derivatives with the customary components of such preparations, such as carriers and additives.

The cosmetic carrier substances can, for a local use, be customary ccarriers such as an ointment base, a powder or primarily a liquid carrier, such as water, alcohol or aqueous-alcoholic mixtures. For this, suitable alcohols include, for example, ethanol, n-propanol, i-propanol, as well as also multivalent alcohols such as glycerine and propylene glycol.

Liquid carrier substances such as water and alcohol are particularly favored, since their use results mostly in clear solutions and these carrier substances come into contact particularly intensively with the scalp.

Preferred preparations effective against dandruff are hair lotions and shampoos, the latter of which contain an anionic, cationic, nonionic or amphoteric detergent as customary wash-active compounds.

As customary additives in the cosmetic preparations, for example, cosmetic resins, emulsifiers, thickeners such as higher fatty alcohols, starch, cellulose derivatives, kerosene, moreover hair care substances such as lanolin derivatives, cholesterin and pantothenic acid, as well as coloring materials, perfume oils, solid filler materials, propellant gas and others come into consideration.

The novel features which are considered as characteristic for the invention are set forth in particular in the appended claims. The invention itself, however, both as to its composition and its method of use, together with additional objects and advantages thereof, will be best understood from the following description of specific embodiments.

DESCRIPTION OF THE PREFERRED EMBODIMENTS

The following examples should more precisely illustrate the subject of the invention.

EXAMPLE 1-SHAMPOO

| | |
|---|---|
| 1.5 g | oligohexamethylene biguanide hydrochloride (n = 4 to 6) |
| 30.0 g | sodium lauryl alcohol diglycol-ether sulfate, 28% aqueous solution |
| 2.0 g | sodium chloride |
| 0.2 g | perfume oil |
| 66.3 g | water |
| 100.0 g | |

EXAMPLE 2-HAIR LOTION

| | |
|---|---|
| 2.0 g | oligohexamethylene biguanide hydrochloride (n = 4 to 6) |
| 40.0 g | isopropanol |
| 0.2 g | perfume oil |
| 0.1 g | coloring agent |
| 57.7 g | water |
| 100.0 g | |

EXAMPLE 3-HAIR SETTING PREPARATION

| | |
|---|---|
| 1.0 g | oligotetramethylene biguanide hydrochloride (n = 4 to 6) |
| 3.0 g | copolymer of 60% vinyl pyrrolidone and 40% vinyl acetate, in powder form |
| 40.0 g | ethanol |
| 0.2 g | perfume oil |
| 0.1 g | coloring agent |
| 55.7 g | water |
| 100.0 g | |

EXAMPLE 4-HAIR DRESSING GEL

| | |
|---|---|
| 2.0 g | 1-methyl biguanide hydrochloride |
| 29.4 g | oleyl cetyl alcohol, oxethylated with 7-8 mole ethylene oxide, 80% (Eumulgen M8 from the Henkel Firm) |
| 17.5 g | paraffin oil |
| 0.2 g | perfume oil |
| 0.1 g | coloring agent |
| 50.8 g | water |
| 100.0 g | |

All of the percentages given in the present application are amounts in percent by weight.

It will be understood that each of the elements described above, or two or more together, may also find a useful application in other types of cosmetic agents differing from the types described above.

While the invention has been illustrated and described as embodied in cosmetic agents for the control of head dandruff containing salts of biguanide derivatives, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method for the treatment of dandruff, comprising applying to the scalp of an individual requiring such treatment an effective amount of a pharmaceutically acceptable lotion, cream, gel or shampoo containing as an active ingredient, from about 1.0% by weight to about 5.0% by weight of a compound represented by the formula

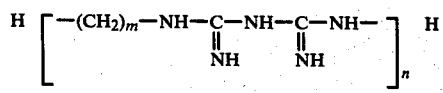

wherein m is from 1 to 10 and n is from 1 to 6 or the hydrochloride thereof.

2. The method of claim 1, wherein said compound is oligohexamethylene biguanide hydrochloride with n from 4 to 6.

3. The method of claim 1, wherein said compound is 1-methyl biguanide hydrochloride.

4. A method for the treatment of dandruff, comprising applying to the scalp of an individual requiring such treatment an effective amount of a pharmaceutically acceptable lotion containing (a) an alcohol selected from ethanol and isopropanol,
(b) water and
(c) as an active ingredient from about 0.1% by weight to about 2.0% by weight of a compound represented by the formula

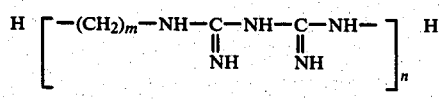

wherein m is from 1 to 10 and n is from 1 to 6 or the hydrochloride thereof.

5. A method for the treatment of dandruff, comprising applying to the scalp of an individual requiring such treatment an effective amount of a pharmaceutically acceptable shampoo containing (a) sodium lauryl alcohol diglycol-ether sulfate, 28 % aqueous solution,
(b) sodium chloride,
(c) water and
(d) as an active ingredient from about 0.1% by weight to about 3.0% by weight of a compound represented by the formula

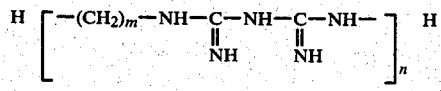

wherein m is from 1 to 10 and n is from 1 to 6 or the hydrochloride thereof.

* * * * *

UNITED STATES PATENT AND TRADEMARK OFFICE
CERTIFICATE OF CORRECTION

PATENT NO. : 4,405,645
DATED : September 20, 1983
INVENTOR(S) : ROTHLISBERGER et al.

It is certified that error appears in the above—identified patent and that said Letters Patent is hereby corrected as shown below:

Claim 4, line 7, "change 0.1%" to -- 1.0% --.

Claim 5, line 9, change "0.1%" to -- 1.0% --.

Signed and Sealed this

Seventh Day of February 1984

[SEAL]

Attest:

GERALD J. MOSSINGHOFF

Attesting Officer    Commissioner of Patents and Trademarks